US006689917B2

(12) United States Patent
Noda et al.

(10) Patent No.: US 6,689,917 B2
(45) Date of Patent: Feb. 10, 2004

(54) PROCESS FOR THE PREPARATION OF PERFLUOROALKANONES

(75) Inventors: Kouzou Noda, Settsu (JP); Hirokazu Aoyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/257,383

(22) PCT Filed: Apr. 20, 2001

(86) PCT No.: PCT/JP01/03382

§ 371 (c)(1),
(2), (4) Date: Oct. 18, 2002

(87) PCT Pub. No.: WO01/81287

PCT Pub. Date: Nov. 1, 2001

(65) Prior Publication Data

US 2003/0144557 A1 Jul. 31, 2003

(30) Foreign Application Priority Data

Apr. 21, 2000 (JP) .................................... 2000-121451

(51) Int. Cl.$^7$ .............................................. C07C 45/48
(52) U.S. Cl. .................... 568/361; 568/364; 568/404; 568/407
(58) Field of Search ................... 568/361, 364, 568/404, 407

(56) References Cited

U.S. PATENT DOCUMENTS

| 3,321,515 A | | 5/1967 | Moore et al. ................ 260/544 |
| 4,136,121 A | | 1/1979 | Martini et al. .............. 260/593 |
| 4,835,318 A | * | 5/1989 | Kruse et al. ................. 568/319 |
| 5,998,671 A | | 12/1999 | Van Der Puy ............... 568/411 |

FOREIGN PATENT DOCUMENTS

JP 1-226846 9/1989
JP 05-017388 1/1993

OTHER PUBLICATIONS

"Dieckmann reaction of dibasic perfluorocarboxylic acid esters.".

Alekseenko, A.N. et al., Ukr. Khim. Zh. (Russian Edition), 54(1), pp. 66–71 (1988).

Adcock, J. et al., "Aerosol direct fluorination. Indirect syntheses of perfluorocyclic ketones," J. Org. Chem., 49(1), pp. 191–193 (1984).

Camaggi, G. et al., "Photochemical isomerisatation derivatives of decafluorocyclohexene and their reactions," J. Chem. Soc. (C), pp. 925–936 (1971).

Holub, F. et al., "The action of elementary fluorine upon organic compounds. XV. Fluorine and cobaltic fluoride as fluorinating agents for ketones," J. Amer. Chem. Soc., 72, pp. 4879–4884 (1950).

* cited by examiner

*Primary Examiner*—John Richter
*Assistant Examiner*—Sikarl A. Witherspoon
(74) *Attorney, Agent, or Firm*—Armstrong, Kratz, Quintos, Hanson & Brooks, LLP

(57) ABSTRACT

The present invention provides a process for producing a linear perfluoroalkanone or a perfluorocycloalkanone, which comprises using as a starting material a combination of the same or different kinds of compounds that are selected from perfluoroalkanoyl halides represented by the formula: $F(CF_2)_nCOX$ wherein X is F, Cl, Br or I and n is an integer of 1 to 8, or a perfluoroalkanedioyl dihalide represented by the formula: $XOC(CF_2)_nCOX$ wherein X is F, Cl, Br or I and n is an integer of 3 to 8, and reacting the starting material with a metal carbonate or metal carbonates. According to the present invention, perfluoroalkanones can be produced with a good yield from relatively easily available starting materials by a simple synthesis method.

6 Claims, No Drawings

PROCESS FOR THE PREPARATION OF PERFLUOROALKANONES

TECHNICAL FIELD

The present invention relates to a process for producing linear or cyclic perfluoroalkanones.

BACKGROUND ART

Perfluoroalkanones are compounds useful as intermediates of fluorine-containing compounds or as dry etching gases. The following methods are known for producing linear or cyclic perfluoroalkanones.

(1) A method for synthesizing octafluorocyclopentanone that comprises subjecting perfluoro-(methylenecyclopentene) to photochlorination, and then to oxidation using potassium permanganate (Camaggi, G. et al., J. Chem. Soc. C, 925–936 (1971)).
(2) A method that comprises treating a starting material such as perfluoromethylenecycloalkene epoxide and perfluoropropylene epoxide with an acid or the like (alumina, cesium fluoride, a Lewis acid and the like) (U.S. Pat. No. 3,321,515).
(3) A method that comprises subjecting cyclopentanone, methylethylketone or the like to direct fluorination (Fred F. Holub et al., J. Amer. Chem. Soc., 72 4879–4884 (1950)).
(4) A method that comprises subjecting methoxycycloalkanone to direct fluorination and treating the resulting compound with sulfuric acid (Adcock, James L. et al., J. Org. Chem., 49(1), 191–193 (1984)).
(5) A method that comprises subjecting ethyl octafluoroheptanedioate, ethyl octafluorooctanedioate, methyl tridecafluoroheptanoate or the like to Dieckmann condensation to synthesize a diol, and then subjecting the diol to a dehydration reaction using phosphorus pentoxide (Alekseenko, A. N. et al., Ukr. Khim. Zh. (Russ. Ed.), 54 (1), 66–71 (1988)).
(6) A method for synthesizing a perfluoroalkanone that comprises promoting a decarboxylation reaction between a metal salt of perfluoroalkanoic acid and a perfluoroalkanoic anhydride (Michael. Van. Der. Puy et al., U.S. Pat. No. 5,998,671).

These conventional methods, however, have problems, such as a low yield of the desired perfluoroalkanones and difficulty in obtaining starting materials.

DISCLOSURE OF THE INVENTION

A principal object of the present invention is to provide a process for synthesizing perfluoroalkanones with a high yield using relatively easily available starting materials by a simple synthesis method.

The inventors of the present invention conducted extensive research to attain the above-mentioned object. As a result, they found that when using as a starting material a combination of the same or different kinds of compounds that are selected from perfluoroalkanoyl halides represented by a specific formula, and reacting the starting material with a metal carbonate, an intermolecular reaction occurs between the starting perfluoroalkanoyl halide and a carbanion produced by decarboxylation of the acid halide, thereby synthesizing a linear perfluoroalkanone with a high yield. Moreover, the inventors found that when a starting material of a perfluoroalkanedioyl dihalide represented by a specific formula is reacted with a metal carbonate, a similar reaction to the above-mentioned reaction occurs intramolecularly, thereby synthesizing a perfluorocycloalkanone with a high yield. This invention is completed based on these findings.

Specifically, the present invention provides the following processes for producing a linear perfluoroalkanone and for producing a perfluorocycloalkanone.
1. A process for producing a linear perfluoroalkanone comprising:
   reacting a starting material with a metal carbonate or metal carbonates to perform an intermolecular reaction of the starting material,
   the starting material being a combination of the same or different kinds of compounds that are selected from perfluoroalkanoyl halides represented by the formula: $F(CF_2)_nCOX$ wherein X is F, Cl, Br or I and n is an integer of 1 to 8.
2. The process for producing a linear perfluoroalkanone according to Item 1 above, wherein the perfluoroalkanoyl halides are compounds selected from perfluoroalkanoyl chlorides and perfluoroalkanoyl fluorides.
3. A process for producing a perfluorocycloalkanone comprising:
   reacting a metal carbonate or metal carbonates with a perfluoroalkanedioyl dihalide represented by the formula: $XOC(CF_2)_nCOX$ wherein X is F, Cl, Br or I and n is an integer of 3 to 8 to perform an intramolecular reaction of the perfluoroalkanedioyl dihalide.
4. The process for producing a perfluorocycloalkanone according to Item 3 above, wherein at least one compound selected from perfluoroalkanedioyl dichlorides and perfluoroalkanedioyl difluorides is used as the perfluoroalkanedioyl dihalide.
5. The process for producing a linear perfluoroalkanone according to Item 1 or 2 above, wherein the reaction is carried out in an aprotic solvent.
6. The process for producing a perfluorocycloalkanone according to Item 3 or 4, wherein the reaction is carried out in an aprotic solvent.

In the process for producing a linear perfluoroalkanone of the present invention, as a starting material, a combination of the same or different kinds of compounds is used that are selected from perfluoroalkanoyl halides represented by the formula: $F(CF_2)_nCOX$ wherein X is F, Cl, Br or I and n is an integer of 1 to 8. Examples of such perfluoroalkanoyl halides include perfluoroalkanoyl chlorides, perfluoroalkanoyl fluorides, perfluoroalkanoyl bromides and the like. Among the above examples, from the standpoint of easy availability, perfluoroalkanoyl chlorides, perfluoroalkanoyl fluorides and the like are preferable. When using different kinds of compounds selected from the above-mentioned perfluoroalkanoyl halides, two or more kinds of compounds can be used.

In the process for producing a perfluorocycloalkanone of the present invention, a perfluoroalkanedioyl dihalide is used as a starting material, which is represented by the formula: $XOC(CF_2)_nCOX$ wherein X is F, Cl, Br or I and n is an integer of 3 to 8. Examples of such perfluoroalkanedioyl dihalides include perfluoroalkanedioyl dichlorides, perfluoroalkanedioyl difluorides, perfluoroalkanedioyl dibromides and the like. Among the above examples, from the standpoint of easy availability, perfluoroalkanedioyl dichlorides, perfluoroalkanedioyl difluorides and the like are particularly preferable. The perfluoroalkanedioyl dihalides can be used alone, or two or more of them can be used.

Among the above-mentioned starting materials, perfluoroalkanoyl fluoride and perfluoroalkanedioyl difluoride are easily obtainable by reacting fuming sulfuric acid with iodide compound ($F(CF_2)_{n+1}I$) and diiodide compound ($IF_2C(CF_2)_nCF_2I$), respectively. Also, perfluoroalkanoyl chloride and perfluoroalkanedioyl dichloride are easily obtainable by reacting thionyl chloride, phosphorus oxychloride, phosphorus pentachloride or the like with the corresponding perfluoroalkanoic acid and perfluoroalkanedioic acid, respectively.

The metal carbonates for use in the present invention include sodium carbonate, potassium carbonate, calcium carbonate, lithium carbonate, strontium carbonate, barium carbonate, aluminum carbonate, and so forth. Among them, sodium carbonate, potassium carbonate and the like are particularly preferable. These metal carbonates can be used alone, or two or more of them can be used in combination.

In the process for producing a linear perfluoroalkanone of the present invention, a combination of the same or different kinds of compounds that are selected from perfluoroalkanoyl halides represented by the above formula is used as a starting material, and a metal carbonate is reacted with the starting material to produce the linear perfluoroalkanone by a decarboxylation reaction. Also the process for producing a perfluorocycloalkanone employs a decarboxylation reaction caused by reacting a metal carbonate with a perfluoroalkanedioyl dihalide represented by the above formula.

In the process for producing a linear perfluoroalkanone and the process for producing a perfluorocycloalkanone of the present invention, in the case of using the metal carbonate of monovalent metal, the amount of the metal carbonate is preferably about 1 to 5 moles and more preferably about 1.5 to 3 moles, per 1 mole of the starting material, i.e., perfluoroalkanoyl halide or perfluoroalkanedioyl dihalide. In the case of using the metal carbonate of divalent metal, the amount of the metal carbonate is preferably about 0.5 to 2.5 moles, and more preferably about 0.75 to 1.5 moles, per 1 mole of the starting material. In the case of using the metal carbonate of a trivalent metal, the amount of the metal carbonate is about 0.5 to 2 moles, and more preferably about 0.5 to 1 mole, per 1 mole of the starting material.

The above-mentioned processes for producing a linear perfluoroalkanone and for producing a perfluorocycloalkanone are each preferably carried out in a solvent. The solvent used in the each process is preferably an aprotic polar solvent. Specific examples of the aprotic polar solvent include monoglyme (ethylene glycol dimethyl ether), diglyme (diethylene glycol dimethyl ether), triglyme (triethylene glycol dimethyl ether), tetraglyme (tetraethylene glycol dimethyl ether) and the like glymes; dimethylformamide, N-methylpyroridone and the like amides; and dimethyl sulfoxide and the like. Among them, the glymes are particularly preferable. The use of the aprotic solvent can promote a smooth reaction and, particularly, suppress the formation of $F(CF_2)_nH$ compound byproduct.

The amount of the solvent for use in the invention is not particularly limited, but preferably 2 to 20 times as much as that of the metal carbonate with respect to weight to promote a smooth reaction.

The method for carrying out the reaction is not particularly restricted, and includes a method comprising the steps of placing a solvent and a metal carbonate into a reactor, increasing a temperature to a predetermined reaction temperature, adding dropwise a starting material, i.e., perfluoroalkanoyl halide or perfluoroalkanedioyl dihalide, to produce a metal salt of a carboxylic acid and then promoting a decarboxylation reaction at a predetermined reaction temperature; a method comprising the steps of placing a solvent and a metal carbonate into a reactor, increasing a temperature to a predetermined reaction temperature, adding dropwise a starting material, i.e., perfluoroalkanoyl halide or perfluoroalkanedioyl dihalide, to produce a metal salt of a carboxylic acid while simultaneously causing a decarboxylation reaction; and like methods. According to the above methods, the desired linear perfluoroalkanone or perfluorocycloalkanone can be produced.

In the above-mentioned reaction, the metal salt is produced preferably at a temperature of about 80 to 210° C., and more preferably about 100 to 155° C. The decarboxylation reaction occurs at a temperature of 155° C. or higher, so it is necessary to increase the reaction temperature to 155° C. or higher to obtain the desired product by the decarboxylation reaction, and the reaction temperature is preferably increased to a temperature of 155 to 210° C., and more preferably to a temperature of about 160 to 190° C.

As to a low boiling product among the reaction product, i.e., linear perfluoroalkanone or perfluorocycloalkanone, when the product accumulates in a reaction system in a large amount, the reaction temperature is not elevated, thereby making it difficult to perform the reaction. Thus, the reaction is preferably carried out while separating the reaction product, i.e., linear perfluoroalkanone or perfluorocycloalkanone, from the reaction system by distillation or the like method.

According to the process of the present invention, octafluorocyclopentanone can be synthesized with a good yield using relatively easily available starting material by a simple synthesis method.

BEST MODE FOR CARRYING OUT THE INVENTION

The present invention will be illustrated in more detail in the following examples.

Example 1

A 300-ml three-necked flask was equipped with a thermometer, a 50-ml dropping funnel, and a simple distillation apparatus for the separation of a reaction product. Into this reactor, were placed 100 ml of triglyme and 10.3 g (97 mmol) of sodium carbonate. A temperature of the solution was increased to 135° C. while stirring, and 22 g (67 mmol) of octafluoroadipoyl dichloride was added dropwise over 3 hours. Thereafter, the reaction temperature was increased to 150° C. and the mixture was stirred with heating at that temperature for 2 hours to produce metal salts. Then the temperature was further increased to 190° C. to promote a decarboxylation reaction and that temperature was maintained for 30 minutes. During the reaction, the reaction product was separated from the reaction system using the simple distillation apparatus and collected with a dry ice-acetone bath. The collected reaction product weighed 13.7 g, and as analyzed by gas chromatography, the octafluorocyclopentanone content in the reaction product was 90%.

Example 2

A reaction was carried out in the same manner as in Example 1 except that 18.5 g (134 mmol) of potassium carbonate was used instead of sodium carbonate. 13.9 g of the reaction product was obtained, and the octafluorocyclopentanone content in the reaction product was 95%.

Example 3

A reaction was carried out in the same manner as in Example 1 except that 17.7 g (67 mmol) of octafluoroadipoyl difluoride was used instead of octafluoroadipoyl dichloride. 13.5 g of the reaction product was obtained, and the octafluorocyclopentanone content in the reaction product was 96%.

Example 4

A 300-ml three-necked flask was equipped with a thermometer, a 50-ml dropping funnel, and a simple distillation apparatus for the separation of a reaction product. Into this reactor, were placed 100 ml of triglyme and 14.8 g (140 mmol) of sodium carbonate. A temperature of the solution was increased to 155° C. while stirring, 22 g (67 mmol) of octafluoroadipoyl dichloride was added dropwise over 3 hours, and a reaction for producing metal salt and a decarboxylation reaction were carried out simultaneously. Thereafter, the temperature was further increased to 190° C. and that temperature was maintained for 30 minutes. During the reaction, the reaction product was separated from the reaction system using the simple distillation apparatus and collected with a dry ice-acetone bath. The collected reaction product weighed 13.9 g and, as analyzed by gas chromatography, the octafluorocyclopentanone content in the reaction product was 95%.

Example 5

A 300-ml four-necked flask was equipped with a thermometer, a 50-ml dropping funnel, and a simple distillation apparatus for the separation of a reaction product. Into this reactor, were placed 100 ml of triglyme and 14.8 g (140 mmol) of sodium carbonate. A temperature of the solution was increased to 150° C. while stirring, and 17.8 g (134 mmol) of trifluoroethanoyl chloride was added dropwise over 3 hours to promote a reaction for producing metal salt. Thereafter, a decarboxylation reaction was carried out while increasing the temperature to 190° C. and that temperature was maintained for 30 minutes. During the reaction, the reaction product was separated from the reaction system using the simple distillation apparatus and collected with a dry ice-acetone bath. The collected reaction product weighed 17.9 g and, as analyzed by gas chromatography, the perfluoropentanone content in the reaction product was 89%.

Example 6

A reaction was carried out in the same manner as in Example 5 except that 15.6 g (134 mmol) of trifluoroethanoyl fluoride was used instead of trifluoroethanoyl chloride. 10.3 g of the reaction product was obtained, and the perfluoropentanone content in the reaction product was 92%.

Example 7

A reaction was carried out in the same manner as in Example 5 except that 44.5 g (134 mmol) of undecafluorohexanoyl chloride was used instead of trifluoroethanoyl chloride. 36.0 g of the reaction product was obtained, and the perfluoroundecanone content in the reaction product was 95%.

Example 8

A 300-ml four-necked flask was equipped with a thermometer, a 50-ml dropping funnel, and a simple distillation apparatus for the separation of a reaction product. Into this reactor, were placed 100 ml of triglyme and 14.8 g (140 mmol) of sodium carbonate. A temperature of the solution was increased to 150° C. while stirring, and 8.9 g (67 mmol) of trifluoroethanoyl chloride and 12.2 g (67 mmol) of pentafluoropropanoyl chloride were simultaneously added dropwise over 2 hours, and then the temperature was increased to 190° C. and that temperature was maintained for 30 minutes. During the reaction, the reaction product was separated from the reaction system using the simple distillation apparatus and collected with a dry ice-acetone bath. The collected reaction products weighed 11.6 g and, as analyzed by gas chromatography, the perfluoroheptanone content in the reaction product was 88%.

What is claimed is:

1. A process for producing a linear perfluoroalkanone comprising:

reacting a starting material with a metal carbonate or metal carbonates to perform an intermolecular reaction of the starting material, the starting material being a combination of the same or different kinds of compounds that are selected from perfluoroalkanoyl halides represented by the formula: $F(CF_2)_nCOX$ wherein X is F, Cl, Br or I and n is an integer of 1 to 8.

2. The process for producing a linear perfluoroalkanone according to claim 1, wherein the perfluoroalkanoyl halides are compounds selected from perfluoroalkanoyl chlorides and perfluoroalkanoyl fluorides.

3. A process for producing a perfluorocycloalkanone comprising:

reacting a metal carbonate or metal carbonates with a perfluoroalkanedioyl dihalide represented by the formula: $XOC(CF_2)_nCOX$ wherein X is F, Cl, Br or I and n is an integer of 3 to 8 to perform an intramolecular reaction of the perfluoroalkanedioyl dihalide.

4. The process for producing a perfluorocycloalkanone according to claim 3, wherein at least one compound selected from perfluoroalkanedioyl dichlorides and perfluoroalkanedioyl difluorides is used as the perfluoroalkanedioyl dihalide.

5. The process for producing a linear perfluoroalkanone according to claim 1 or 2, wherein the reaction is carried out in an aprotic solvent.

6. The process for producing a perfluorocycloalkanone according to claim 3 or 4, wherein the reaction is carried out in an aprotic solvent.

* * * * *